(12) United States Patent
Bombardelli et al.

(10) Patent No.: US 7,057,078 B2
(45) Date of Patent: Jun. 6, 2006

(54) HYPERFORIN HALOGENATED DERIVATIVES, THE USE THEREOF AND FORMULATIONS CONTAINING THEM

(75) Inventors: Ezio Bombardelli, Milan (IT); Paolo Morazzoni, Milan (IT); Antonella Riva, Milan (IT); Nicola Fuzzati, Milan (IT)

(73) Assignee: INDENA S.p.A., Milan (IT)

( * ) Notice: Subject to any disclaimer, the term of this patent is extended or adjusted under 35 U.S.C. 154(b) by 0 days.

(21) Appl. No.: 10/511,894

(22) PCT Filed: Apr. 15, 2003

(86) PCT No.: PCT/EP03/03923

§ 371 (c)(1),
(2), (4) Date: May 31, 2005

(87) PCT Pub. No.: WO03/091193

PCT Pub. Date: Nov. 6, 2003

(65) Prior Publication Data

US 2005/0222274 A1    Oct. 6, 2005

(30) Foreign Application Priority Data

Apr. 23, 2002   (IT)   .......................... M12002A0871

(51) Int. Cl.
*C07C 49/00* (2006.01)
*A61K 31/11* (2006.01)
*A61K 31/05* (2006.01)

(52) U.S. Cl. ...................... 568/375; 568/377; 514/698; 514/732

(58) Field of Classification Search ................... None
See application file for complete search history.

(56) References Cited

U.S. PATENT DOCUMENTS 6,322,824 B1 * 11/2001 Chatterjee et al. .......... 424/730
6,444,662 B1 * 9/2002 Chatterjee et al. ..... 514/210.01
6,656,510 B1 * 12/2003 Bombardelli et al. ....... 424/730

FOREIGN PATENT DOCUMENTS

| WO | WO 99 41220 | 8/1999 |
|---|---|---|
| WO | WO 99 64388 | 12/1999 |

* cited by examiner

*Primary Examiner*—Sikarl A. Witherspoon
(74) *Attorney, Agent, or Firm*—Young & Thompson

(57) ABSTRACT

Hyperforin and adhyperforin halogenated derivatives of general formula (I) in which X, R and $R_1$ have the meanings as defined in the disclosure, the process for the preparation thereof and the use thereof in the pharmaceutical and/or nutritional field, in particular in the treatment of depression, and Alzheimer's disease.

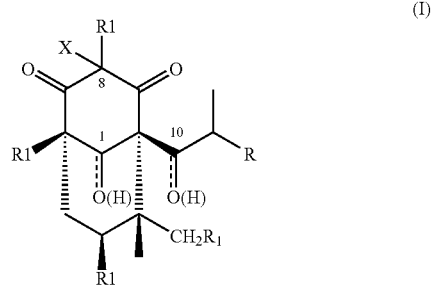

(I)

9 Claims, No Drawings

HYPERFORIN HALOGENATED DERIVATIVES, THE USE THEREOF AND FORMULATIONS CONTAINING THEM

FIELD OF THE INVENTION

The present invention relates to hyperforin and adhyperforin halogenated derivatives and the use thereof in the pharmaceutical and/or nutritional field, in particular in the treatment of depression and Alzheimer's disease.

TECHNOLOGICAL BACKGROUND

Flowering tops of *Hypericum perforatum* contain a number of classes of structurally different substances that act directly or indirectly on the central nervous system. The mechanisms of action of these compounds are different and comprise anti-MAO action (Suzuki O R. et al. Planta Med., 272–4, 1984), action on serotonin release and re-uptake (Muller W. E. et al Pharmacopsychiatry, 30, 102–107, 1997) and benzodiazepine-like activity (Coot J. M. Pharmacopsychiatry 30,108–112, 1997).

Hyperforin, a floroglucin derivative, is one of the main components of the lipophilic fraction of *Hypericum perforatum* flowering tops; said fraction also contains adhyperforin, a hyperforin higher homologue, although in lower concentration (Erdelmeier C. A. J., Pharmacopsychiatry, 31, 2–6, 1998).

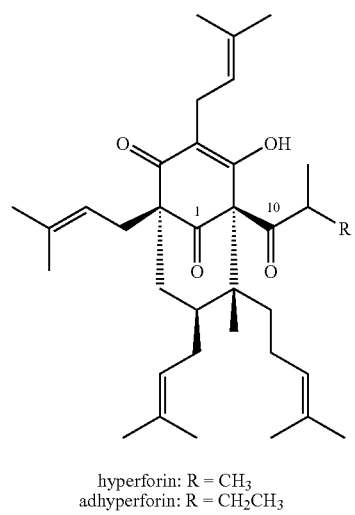

hyperforin: R = CH₃
adhyperforin: R = CH₂CH₃

Hyperforin has recently been the object of numerous studies that establish its important role as an antidepressant (Pharmacopsychiatry, 31 Suppl.1, 1–60. 1998). Furthermore, it is recognized that the extracts of *Hypericum perforatum* can be used for the prophylaxis and treatment of neurodegenerative diseases, inter alia Alzheimer's disease (WO/9940905, WO0057707). In particular, hyperforin and adhyperforin salts with inorganic cations or ammonium salts were described for this purpose (WO9941220).

It is known from literature that hyperforin is poorly stable in the usual extraction and storage conditions; according to WO 97/13489, the hyperforin content in a St. John's Wort water-alcoholic extract falls already after a few weeks. WO 97/13489 further recites that, in order to obtain hyperforin stable extracts, antioxidants should be present during the whole work up (extraction, purification and storage). It is therefore evident that the high instability of hyperforin makes the preparation of hyperforin pharmaceutical formulations quite difficult. In order to obviate to said drawback, compounds more stable than hyperforin, such as the salts disclosed in WO 99/41220 and the hydroxy-functionalized derivatives (WO 99/64388) cited above, have recently been prepared.

It is moreover known (Bystrov et al., Bioorg. Khim, 1978) that hyperforin and adhyperforin can be transformed into the corresponding octahydroderivatives, (IIa and IIb) by catalytic reduction of the isoprene side chains

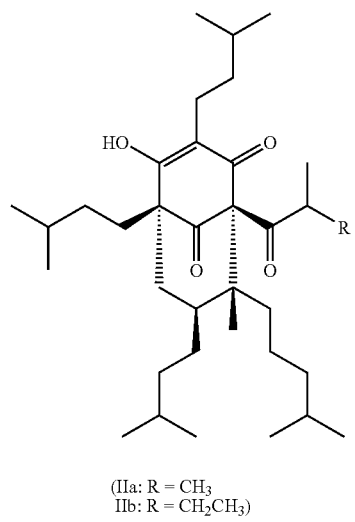

(IIa: R = CH₃
IIb: R = CH₂CH₃)

or into the corresponding tetrahydroderivatives (IIc and IId), by reduction of the keto groups at the 1- and 10-positions to hydroxy groups

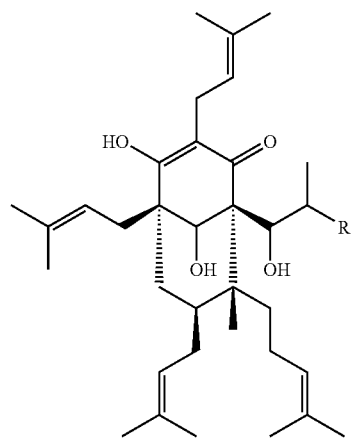

(IIc: R = CH₃
IId: R = CH₂CH₃)

DETAILED DISCLOSURE OF THE INVENTION

It has now been found that the compounds obtained by introducing a halogen at the 8-position of hyperforin, adhyperforin or reduction derivatives thereof possess antidepressant, anxiolytic and anti-neurodegenerative activities surprisingly higher than hyperforin and adhyperforin.

The present invention specifically relates to compounds of formula (I)

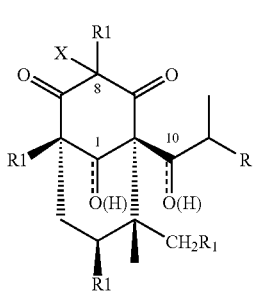

(I)

wherein X is a halogen atom, R is methyl or ethyl and, alternatively:

a) $R_1$ is 3-methyl-2-buten-1-yl and oxo groups are present at the 1- and 10-positions;

b) $R_1$ is 3-methyl-but-1-yl and oxo groups are present at the 1- and 10-positions;

c) $R_1$ is 3-methyl-2-buten-1-yl and hydroxy groups are present at the 1- and 10-positions;

d) $R_1$ is 3-methyl-but-1-yl and hydroxy groups are present at the 1- and 10-positions;

and the pharmaceutically acceptable salts or esters thereof.

The term "halogen" herein means fluorine or a halogen selected from chlorine, bromine and iodine, more preferably chlorine and bromine, most preferably chlorine.

Moreover, for the purposes of the present disclosure, "octahydro" means hyperforin or adhyperforin derivatives in which $R_1$ is 3-methyl-but-1-yl and oxo groups are present at the 1 and 10 positions; "tetrahydro" means hyperforin or adhyperforin derivatives in which $R_1$ is 3-methyl-2-buten-1-yl and hydroxy groups are present at the 1 and 10 positions; "dodecahydro" means hyperforin or adhyperforin derivatives in which $R_1$ is 3-methyl-but-1-yl and hydroxy groups are present at the 1 and 10 positions.

Preferred compounds according to the invention are the compounds of formula (I) in which: X is a chlorine or bromine atom, R is methyl or ethyl, $R_1$ is 3-methyl-2-buten-1-yl and oxo groups are present at the 1 and 10 positions (in the following defined as: 8-chlorohyperforin Ia, 8-chloroadhyperforin Ib, 8-bromohyperforin Ic, 8-bromoadhyperforin Id)

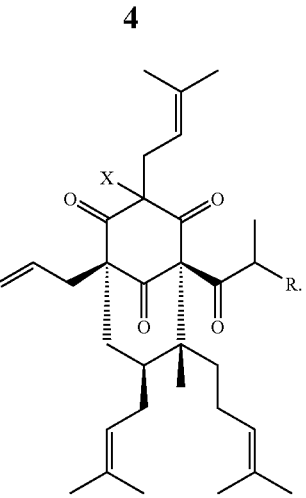

(Ia: X = Cl, R = $CH_3$
Ib: X = Cl, R = $CH_2CH_3$
Ic: X = Br, R = $CH_3$
Id: X = Br, R = $CH_2CH_3$)

Furthermore, preferred compounds of formula (I) are those wherein: X is a chlorine or bromine atom, R is methyl or ethyl, $R_1$ is 3-methyl-but-1-yl and oxo groups are present at the 1 and 10 positions (in the following defined as: 8-chlorooctahydrohyperforin Ie, 8-chlorooctahydroadhyperforin If, 8-bromooctahydrohyperforin Ig, 8-bromooctahydroadhyperforin Ih)

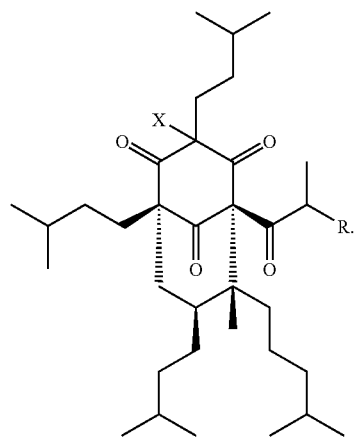

(Ie: X = Cl, R = $CH_3$
If: X = Cl, R = $CH_2CH_3$
Ig: X = Br, R = $CH_3$
Ih: X = Br, R = $CH_2CH_3$)

Particularly preferred are 8-chlorohyperforin (Ia) and 8-chlorooctahydrohyperforin (Ie).

Compounds of formula (I) are prepared by reacting hyperforin, adhyperforin or a tetra-, octa-, dodecahydro derivative thereof with a suitable halogenating agent, preferably with N-chlorosuccinimide or N-bromosuccinimide.

Tetrahydroderivatives (IIa) and (IIb) as mentioned above are obtained by reduction of the keto groups with hydrides, selected for example from $NaBH_4$, Redal®, Vitride®, $LiAlH_4$.

Octahydroderivatives (IIc) and (IId) as above mentioned are obtained by reduction of the isoprene side chains by catalytic hydrogenation, using for example palladium on charcoal or Nickel/Raney.

Dodecahydroderivatives (dodecahydrohyperforin IIe and dodecahydroadhyperforin IIf)

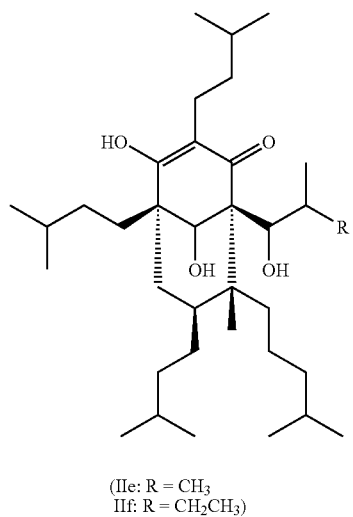

(IIe: R = CH$_3$
IIf: R = CH$_2$CH$_3$)

are obtained from the octahydroderivatives by treatment with hydrides as indicated above.

Dodecaidroderivatives (IIe) and (IIf) are novel compounds and are also part of the present invention.

The process for the preparation of the compounds of the invention starting from the flowering tops of *Hypericum perforatum* can be summarized as follows:

The flowering tops of *Hypericum perforatum* can be extracted with alcohols or aliphatic ketones, either pure or in a mixture thereof with water or with gas in supercritical conditions; the resulting extract is partitioned between n-hexane and aqueous solutions of aliphatic alcohols. The hexane solution is extracted with alkaline methanol to extract hyperforin and adhyperforin. The methanolic solution is acidified, then treated with a weakly basic ion exchange resin, which selectively retains hyperforin and adhyperforin. The resin is eluted with acidic methanol and the eluate is concentrated to small volume, then diluted with water and extracted with n-hexane. The hexane solution is concentrated to small volume and the resulting concentrate is ready for derivatization. The residue is taken up in chlorinated solvents and the suitable reactive is added thereto, according to the procedures reported in the examples.

The present invention further relates to the use of derivatives of formula (I) and the pharmaceutically acceptable salts or esters thereof for the preparation of medicaments for the therapy of depression, and Alzheimer's disease.

Compounds of formula (I), in particular 8-chloro and 8-bromo hyperforin and 8-chloro and 8-bromo adhyperforin, have shown antidepressant effect.

The antidepressant effect of the compounds of the invention was evaluated in the rat by the forced swimming test, evaluating the parameters: struggling, floating and swimming according to what described by Cervo et al. in Neuropharmacology, 26, 14969–72, 1987. The compounds were administered in 3 doses: 30 minutes after the pre-test, 5 hours and 30 minutes before the test. The results reported in the table below prove that the compounds of the invention are more active than parent hyperforin.

| Treatment | mg/Kg | Struggling (sec.) | Floating (sec.) | Swimming (sec.) |
|---|---|---|---|---|
| Carrier | | 7.0 ± 2.4 | 174.5 ± 15.9 | 118.5 ± 15.8 |
| Chlorohyperforin | 3.125 | 46.9 ± 5.9 | 72.1 ± 6.7 | 181.0 ± 11.3 |
| Chlorooctahydro-hyperforin | 6.25 | 57.3 ± 6.2 | 63.4 ± 9.2 | 165.6 ± 12.5 |
| Hyperforin | 6.25 | 30.4 ± 4.6 | 60.4 ± 7.3 | 99.3 ± 10.6 |
| Desipramin | 10 | 148.3 ± 12.6 | 53.0 ± 9.2 | 98.8 ± 7.9 |

The compounds of the invention also proved particularly active against Alzheimer's disease, due to their ability to increase APPs, the soluble, harmless form of Alzheimer Precursor Protein (APP). It is in fact known that proteolytic cleavage of Alzheimer Precursor Protein (APP) is mediated both by β- and γ-secretase, inducing an increased production of amyloid peptide Ab1-42 (which also plays a central role in the appearance of Alzheimer's disease), and α-secretase, giving raise to soluble APPs which have no pathogenic activity (Eslr W. P., Wolfe M. S., Science, 293, 1449–54, 2001).

The effect of the compounds of the invention on the release of APPs produced by α-secretase was evaluated in the culture medium of a neuroblastoma cell line (SH-SY5Y) according to the procedure described by Galbete J. L. et al. in Biochem J. 348, 307–313, 2000.

The results reported in the following table show that the tested compounds activate α-secretase—mediated APP metabolism, inducing an increase in APPs secreted in the culture medium:

| | APPs % |
|---|---|
| Controls | 100 |
| 10 μM Hyperforin | 296 |
| 10 μM Chlorohyperforin | 627 |
| 10 μM Chlorooctahydrohyperforin | 855 |

The compounds of the invention can be formulated according to conventional techniques, for example according to what described in Remington's Pharmaceutical Sciences Handbook, XVII Ed. Mack Pub., N.Y., U.S.A, in the form of soft-gelatin capsules, hard-gelatin capsules, tablets, suppositories; preferably the extract of the invention is formulated in soft-gelatin capsules or in controlled-release formulations. The dosage ranges from 10 to 100 mg per unit dose in the usual formulations and up to 200 mg in the controlled-release formulations, in this case the suggested dose being 200 mg per dose/daily. Furthermore, the compounds can be administered through the controlled-release transdermal route applying the formulation in the proximal area to the cerebral carotid artery derivations. The dosages of compound in these formulations range from 10 to 100 mg per dose/daily.

The examples reported hereinbelow illustrate the invention in greater detail.

EXAMPLES

Example 1

Preparation of Chlorohyperforin 10 kg of flowering tops of *Hypericum perforatum* and 30 L of methanol are extracted in a 50 L extraction plant and the mass is left to stand at room temperature for 3 hrs; the extraction is repeated 3 more times, then the combined extracts are concentrated under vacuum to 5 kg and the concentrate is extracted with 3×5 L of n-hexane. The organic layer is extracted with methanolic KOH until exhaustion of hyperforin and adhyperforin.

This solution is neutralized and filtered through a weakly basic Amberlite resin, which selectively retains hyperforin and adhyperforin; the retained product is eluted again with methanol acidified with phosphoric acid; the methanolic eluate is concentrated under vacuum at 25° C., the diluted water and back-extracted with n-hexane until exhaustion of hyperforin.

The combined organic layers are decolourized with 0.3% charcoal, then dried over $Na_2SO_4$ and concentrated to an oil below 40° C. under vacuum. After solidification the oil yields a wax (0.52 kg) containing approx. 90% of hyperforin.

The residue is taken up in 3 L of $CH_2Cl_2$ and added with 0.14 kg of N-chlorosuccinimide, under strong stirring. The solution is left to stand for three hours under stirring at room temperature, checking the disappearance of hyperforin by TLC using silica gel plates and a n-hexane/ethyl acetate 9:1 mixture as eluent (Rf hyperforin 0.20; chlorohyperforin 0.80). After completion of the reaction, 3 L of water are added; the organic layer is washed with $Na_2S_2O_3$, then dried over $Na_2SO_4$. The solvent is evaporated off, the residue is chromatographed on silica gel eluting with a n-hexane/ethyl acetate 98:2 mixture. The fractions containing the chloroderivative are concentrated separately, thereby obtaining 0.48 kg of product which, after crystallization from petroleum ether, has the following chemical-physical and spectroscopical characteristics: $[a]_D$+16 (c=0.5 $CH_2Cl_2$);

IR $v^{max}$ (KBr) 1722, 1713, 1446, 1377, 1230, 1064, 831 $cm^{-1}$;

$^1$H-NMR (300 MHz $CDCl_3$): 1.41 (m, H-4), 2.16 (m, H-5), 1.70 (m, H-5'), 2.80 (m, H-11), 1.18 (d, J=7 Hz, H-12), 1.02 (d, J=7 Hz, H-13), 1.06 (s, H-14), 2.01 (m, H-15), 1.06 (m, H-15'), 5.03 (m H-17), 1.66 (br s, H-19), 1.60 (br s, H-20), 2.05 (m, H-21), 1.65 (m, H-21'), 4.76 (m, H-22), 1.66 (s, H-24), 1.52 (s, H-25), 3.18 (s, H-26), 4.96 (m, H-27), 1.63 (br s, H-29), 1.69 (br s, H-30), 2.60 (m, H-31), 5.17 (dd, J 13.6, H-32), 1.66 (s, H-35).

$^{13}$C-NMR (75 MHz $CDCl_3$): δ207.6, 205.4, 198.7, 195.9, 139.2, 135.0, 134.1, 131.8, 124.5, 121.8, 118.9, 116.8, 85.1, 67.2, 65.1, 56.2, 45.7, 40.1, 38.5, 37.5, 31.6, 31.5, 28.2, 26.4, 26.1, 26.0, 25.9, 25.5, 22.2, 20.6, 18.6, 18.2, 18.1, 17.9, 13.9.

ESIMS m/z 593, 595 [M+Na$^+$] (100,38), 1163, 1165 [2M+Na$^+$] (32, 28).

The same chromatographic separation also affords, together with the above compound, 0.049 kg of chloradhyperforin having the following chemical-physical and spectroscopical characteristics:

$^1$H-NMR (300 MHz $CDCl_3$): δ5.27–4.75 (4H, m, H-18, H-23, H-28, H-33), 2.23, 3.09 (2-H, dd, J=13.4, 8.4 Hz, $CH_2$-32), 2.63 (2H, m, $CH_2$-27), 2.80–1.42 (10H, m, H-4, H-11, $CH_2$-5, $CH_2$-16, $CH_2$-17, $CH_2$-22), 1.82–(27H, s, $CH_3$-20, $CH_3$-21, $CH_3$-25, $CH_3$-26, $CH_3$-29, $CH_3$-30, $CH_3$-31, $CH_3$-35, $CH_3$-36), 1.21 (3H, d, J=6.6 Hz, $CH_3$-14), 0.87 (3H, d, J=6.6 Hz, $CH_3$-13), 1.07 (3H, s, $CH_3$-15).

$^{13}$C-NMR (75 MHz $CDCl_3$): δ206.9, 205.4, 198.7, 196.7, 139.2, 135.0, 134.1, 131.9, 124.5, 121.8, 118.9, 116.8, 85.1, 67.2, 65.1, 56.2, 46.7, 45.7, 45.2, 37.5, 31.6, 31.5, 28.5, 28.2, 26.4, 26.1, 26.0, 25.9, 25.5, 18.6, 18.2, 18.1, 18.0, 16.8, 13.9, 11.6.

ESIMS m/z 607, 609 [M+Na$^+$] (100, 34), 1191, 1193 [2M+Na$^+$] (21, 20).

Example 2

Preparation of Octahydrohyperforin Dicyclohexylammonium Salt 50 g of hyperforin obtained according to what reported in Example 1 are dissolved in 500 ml of ethyl acetate in the presence of 2 g of 5% palladium on charcoal and hydrogenated until complete hydrogen absorption. The catalyst is filtered off, the hetero-acetic solution is concentrated to dryness under vacuum and the residue is dissolved in n-hexane. The solution is added with a stoichiometric amount of dicyclohexylamine, thereby obtaining sufficiently selective crystallization of the corresponding salt.

62 g of octahydrohyperforin dicyclohexylammonium salt are obtained, having the following spectroscopical characteristics:

$^1$H-NMR (300 MHz $CDCl_3$): δ3.03 (2H, m, CH-DCHA), 2.55–2.30. 2.10–1.76 (20H, m, $CH_2$-DCHA), 1.70–1.10 (22H, m, H-4, H-11, $CH_2$-5, $CH_2$-15, $CH_2$-16, $CH_2$-17, $CH_2$-21, $CH_2$-22, $CH_2$-26, $CH_2$-27, $CH_2$-31, $CH_2$-32), 0.97–0.83 (24H, d, $CH_3$-19, $CH_3$-20, $CH_3$-24, $CH_3$-25, $CH_3$-29, $CH_3$-30, $CH_3$-34, $CH_3$-35), 1.19, 1.12 (6H, d, J=6.5 Hz, $CH_3$-12, $CH_3$-13), 0.91 (3H, s, $CH_3$-14).

$^{13}$C-NMR (75 MHz $CDCl_3$): δ213.1, 211.1, 186.3, 183.6, 119.0, 82.5, 60.8, 53.5, 47.5, 44.2, 41.3, 41.0, 40.9, 38.2, 38.1, 37.8, 33.8, 31.0, 30.7, 30.0, 29.4, 28.8, 28.3, 27.9, 27.1, 25.4, 25.1, 24.9, 23.5, 23.2, 23.1, 22.9, 22.8, 22.7, 22.5, 13.7.

ESIMS m/z 567 [M+Na$^+$] (100), 1111 [2M+Na$^+$] (91).

Example 3

Preparation of Chlorooctahydrohyperforin

A solution of 10 g of dicyclohexylammonium octahydrohyperforinate in 60 ml of methylene chloride is added with 1.89 g of N-chlorosuccinimide and the mixture is left under stirring for 30 min. The organic phase is added with 60 ml of water, washed with a $Na_2S_2O_3$ saturated solution, then dried over $Na_2SO_4$; after concentration to dryness the residue is purified on a silica gel column, eluting the desired compound with an ethyl acetate/hexane 95:5 mixture. The resulting fractions are evaporated to dryness to obtain the desired compound as white powder which, after recrystallization from methanol, yields 6.27 g of chloro derivative having the following spectroscopical characteristics:

$^1$H-NMR (300 MHz CDCl$_3$): δ3.04–1.04 (22H, m, H-4, H-11, CH$_2$-5, CH$_2$-15, CH$_2$-16, CH$_2$-17, CH$_2$-21, CH$_2$-22, CH$_2$-26, CH$_2$-27, CH$_3$-31, CH$_2$-32), 1.05–0.83 (24H, d, CH$_3$-19, CH$_3$-20, CH$_3$-24, CH$_3$-25, CH$_3$-13), CH$_3$-30, CH$_3$-34, CH$_3$-35), 1.19, 1.03 (6H, d, J=6.6 Hz, CH$_3$-12, CH$_3$-13). 1–03 (3H, s, CH$_3$-14).

$^{13}$C-NMR (75 MHz CDCl$_3$): δ207.6, 205.1, 199.3, 195.8, 84.9, 68.7, 64.5, 56.8, 46.1, 43.3, 40.2, 39.9, 38.1, 37.8, 34.8, 33.5, 31.3, 30.7, 29.0, 28.8, 28.2, 27.0, 24.8, 23.0, 22.9, 22.8, 22.7, 22.5, 22.4, 22.1, 20.6, 14.2.

ESIMS m/z 601, 603 [M+Na$^+$] (100.38), 1179, 1181 [2M+Na$^+$] (62, 48).

Example 4

Preparation of Dodecahydrohyperforin 1.72 g of dicyclohexylammonium octahydrohyperforinate (M.W.=716; 2.41 mmol) are dissolved in 20 ml of THF under magnetic stirring; the solution is added with a strong excess (3.5 g) of LiAlH$_4$ (0.092 mol). The progress of the reaction is monitored by TLC (eluent petroleum ether/ EtOAc 9:1 Rfp=0.6; Rfa=0.6; Rfc=0.52; Rfd=0.18). After ten minutes the reaction is completed.

The reactive excess is destroyed according to what described in example 3. The semisolid reaction mixture is filtered and the residue is thoroughly washed with ethyl acetate. The solution is evaporated to dryness, the reaction crude is dissolved in 15 ml of petroleum ether/ethyl ethyl 3:1 and the solution is placed in a 150 ml separatory funnel. The organic phase is washed three times with 2N sulfuric acid and subsequently with brine. The aqueous phase is removed, the organic one is dried over Na$_2$SO$_4$ and concentrated to dryness. The resulting product is purified by column chromatography on 75 g of silica gel, eluting the desired compound with petroleum ether/ethyl acetate 99:1. 0.9 g of dodecahydrohyperforin are obtained, having the following physical-physical and spectroscopical characteristics:

EIMS m/z 548 [M]$^+$.

The invention claimed is:

1. A compound of formula (I)

(I)

wherein X is a halogen atom, R is methyl or ethyl and, alternatively:
   a) R$_1$ is 3-methyl-2-buten-1-yl and oxo groups are present at the 1- and 10-positions;
   b) R$_1$ is 3-methyl-but-1-yl and oxo groups are present at the 1- and 10-positions;
   c) R$_1$ is 3-methyl-2-buten-1-yl and hydroxy groups are present at the 1- and 10-positions;
   d) R$_1$ is 3-methyl-but-1-yl and hydroxy groups are present at the 1- and 10-positions;
   and the pharmaceutically acceptable salts or esters thereof.

2. The compound as claimed in claim 1 wherein X is chlorine or bromine.

3. The compound as claimed in claim 1 wherein X is chlorine.

4. A compound selected from:
   8-chlorohyperforin (Ia), 8-chloroadhyperforin (Ib), 8-bromohyperforin (Ic), 8-bromoadhyperforin (Id)

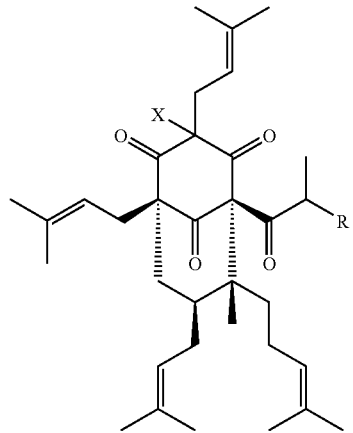

(Ia: X = Cl, R = CH$_3$
Ib: X = Cl, R = CH$_2$CH$_3$
Ic: X = Br, R = CH$_3$
Id: X = Br, R = CH$_2$CH$_3$)

8-chlorooctahydrohyperforin (Ie), 8-chlorooctahydroadhyperforin (If), 8-bromooctahydrohyperforin (Ig), 8-bromooctahydroadhyperforin (Ih)

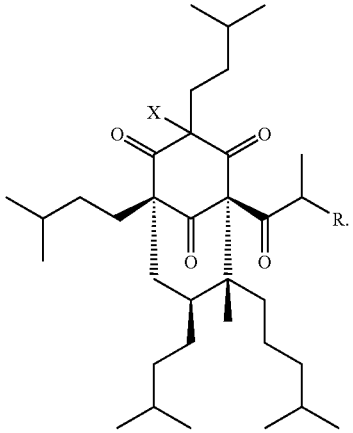

(Ie: X = Cl, R = CH$_3$
If: X = Cl, R = CH$_2$CH$_3$
Ig: X = Br, R = CH$_3$
Ih: X = Br, R = CH$_2$CH$_3$)

5. Compounds according to claim 1 for use as medicament.

6. A pharmaceutical composition containing a compound of claim 1 in mixture with suitable excipients or carriers.

7. A pharmaceutical composition containing a compound of claim 2 in mixture with suitable excipients or carriers.

8. A pharmaceutical composition containing a compound of claim 3 in mixture with suitable excipients or carriers.

9. A pharmaceutical composition containing a compound of claim 4 in mixture with suitable excipients or carriers.

* * * * *